United States Patent [19]

Dutra

[11] 4,340,416

[45] Jul. 20, 1982

[54] N-SUBSTITUTED TRIESTERS OF N-PHOSPHONOMETHYLGLYCINE

[75] Inventor: Gerard A. Dutra, Ladue, Mo.

[73] Assignee: Monsanto Company, St. Louis, Mo.

[21] Appl. No.: 250,525

[22] Filed: Apr. 2, 1981

Related U.S. Application Data

[62] Division of Ser. No. 63,297, Aug. 2, 1979, Pat. No. 4,261,727.

[51] Int. Cl.³ .................... A01N 57/14; C07F 9/40
[52] U.S. Cl. .................................. 71/86; 260/941
[58] Field of Search ............... 71/86; 260/938, 941

[56] References Cited

U.S. PATENT DOCUMENTS 4,120,689 10/1978 Dutra ............................... 71/86
4,197,254 4/1980 Gaertner ........................ 71/86 X

*Primary Examiner*—Catherine L. Mills
*Attorney, Agent, or Firm*—Gordon F. Sieckmann; Howard C. Stanley

[57] ABSTRACT

This disclosure relates to novel N-substituted triesters of N-phosphonomethylglycine which are useful as herbicides. This disclosure further relates to herbicidal compositions containing such N-substituted N-phosphonomethylglycinates and to herbicidal methods employing such compounds and compositions.

12 Claims, No Drawings

N-SUBSTITUTED TRIESTERS OF N-PHOSPHONOMETHYLGLYCINE

This is a division, of application Ser. No. 63,297 filed Aug. 2, 1979, now U.S. Pat. No. 4,261,727.

This invention relates to novel N-substituted triesters of N-phosphonomethylglycine which are useful as herbicides. This invention further relates to herbicidal compositions containing such N-substituted triesters of N-phosphonomethylglycine and to herbicidal methods employing such compounds and compositions. The N-substituted triesters of N-phosphonomethylglycine of the present invention are characterized as having a substituted aminocarbonyl group or an alkoxymalonyl group bonded to the glycine nitrogen.

U.S. Pat. No. 4,120,689 discloses benzyl and aryl esters of N-phosphonomethylglycine of the formula

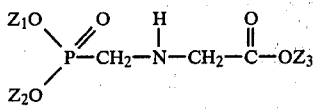

wherein $Z_1$ is selected from the group consisting of phenyl, benzyl, naphthyl, biphenylyl, benzyloxyphenyl, and phenyl, benzyl, or naphthyl groups substituted with from 1 to 3 groups selected from the class consisting of hydroxyl, lower alkyl, lower alkoxy, lower alkylthio, trifluoromethyl, carbo(lower alkoxy), nitro or halo; $Z_2$ is hydrogen or a group represented by $Z_1$; and $Z_3$ is a lower alkyl group, and the strong acid salts of such compounds. Such compounds are useful as herbicides and are prepared by reacting a dibenzyl or diaryl phosphite with a N-methylene alkylglycinate trimer.

U.S. Pat. No. 3,970,695 describes N-trifluoroacetyl derivatives of N-phosphonomethylglycine of the formula

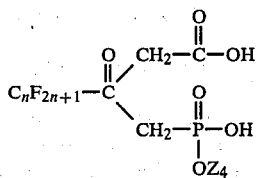

wherein $Z_4$ is a H or a

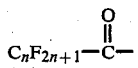

group and n is an integer of from 1 to 4; which are useful as post-emergent herbicides.

U.S. Pat. No. 3,991,095 discloses N-thiolcarbonyl derivatives of N-phosphonomethylglycine and salts thereof of the formula

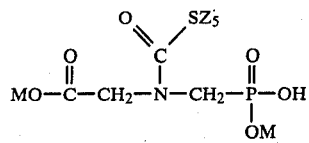

wherein each M is hydrogen, alkali metal, ammonium or lower alkyl hydrocarbon amine, $Z_5$ is lower alkyl, phenyl or benzyl, and said phenyl or benzyl can contain a chlorine, nitro, methyl, methoxy or trifluoromethyl substituent. Herbicidal compositions containing such compounds and herbicidal methods employing such compounds and compositions described in U.S. Pat. No. 4,035,177.

U.S. Pat. No. 3,853,530 describes a method of regulating the growth and development of plants by treating the plant with a compound of the formula

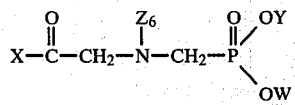

wherein $Z_6$ is selected from the group consisting of hydrogen, formyl, acetyl, benzoyl, nitrobenzoyl, and chlorinated benzoyl; Y and W are each independently selected from the group consisting of hydrogen and lower alkyl; X is selected from the group consisting of hydroxy, alkoxy and chloroalkoxy of up to 12 carbon atoms, lower alkenoxy, cyclohexyloxy, morpholino pyrrolidinyl, piperidino and $NHX^1$; wherein $X^1$ is selected from the group consisting of hydrogen, lower alkyl and alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number up to 30, hydrochloride, pyridine, ammonium, lower aliphatic hydrocarbon amine, lower alkanol amine and aniline.

The compounds of the present invention are represented by the formula

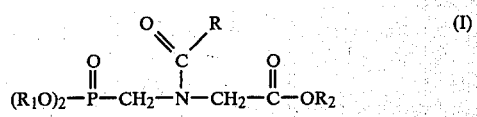

wherein R is selected from the group consisting of morpholino, a

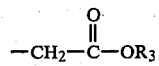

group, wherein $R_3$ is lower alkyl, and a

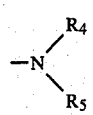

group wherein $R_4$ and $R_5$ are independently selected from the group consisting of lower alkyl, lower alkenyl, benzyl and lower alkylphenylmethyl; $R_1$ is phenyl or lower alkoxyphenyl and $R_2$ is lower alkyl.

As employed herein, the term "lower alkyl" designates those alkyl radicals which have up to four carbon atoms in a straight or branched chain, such as, for example, methyl, ethyl, propyl, isopropyl, butyl, isobutyl, sec-butyl and t-butyl.

Groups illustrative of the "lower alkenyl" radicals represented by $R_4$ and $R_5$ include alkenyl radicals having from 2 to 4 carbons such as vinyl, allyl, propenyl and butenyl.

Illustrative of the "lower alkoxyphenyl" groups which $R_1$ represents are alkoxyphenyl groups wherein the substituent is in the ortho, meta or para position, for example, methoxyphenyl, ethoxyphenyl, propoxyphenyl, butoxyphenyl, t-butoxyphenyl and the like.

Groups illustrative of the substituted amino groups represented by

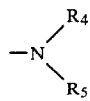

include, for example, dimethylamino, diethylamino, dipropylamino, dibutylamino, N',N'-(methyl)(ethyl)amino, N',N'-(methyl)(butyl)amino, dipropenyl amino, N',N'-(propenyl)(butenyl)amino, N',N'-(methyl)(propenyl)amino, N',N'-(ethyl)(benzyl)amino, N',N'-(propenyl)(benzyl)amino, N',N'-(methyl)[(4-methylphenyl)methyl]amino, N',N'-(ethyl)[(3-propylphenyl)methyl]amino, N',N'-(propenyl)[(2-ethylphenyl)methyl]amino and the like.

In accordance with the present invention, the triester compounds of formula (I) are prepared by reacting a compound of the formula

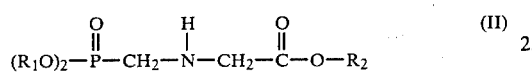

wherein $R_1$ and $R_2$ are above defined; with a carbonyl chloride of the formula

wherein R is above defined; within a temperature range of 0° C. to 100 C. in the presence of a hydrogen chloride acceptor. For ease of reaction and recovery of product, it is preferred to conduct the process of the present invention within a range of 5° C. to 10° C.

The hydrogen chloride acceptor is any amine, preferably a tertiary amine, which forms an amine hydrochloride under the reaction conditions employed in the process of the present invention. Examples of tertiary amine hydrogen chloride acceptors include trimethylamine, triethylamine, tributylamine, trihexylamine, 1,5-diazabicyclo[5.4.0]undec-5-ene, pyridine, quinoline and the like. For ease of reaction and recovery of product it is preferred to employ 1,5-diazabicyclo[5.4.0]undec-5-ene as the hydrogen chloride acceptor.

In preparing the triester compounds of formula (I), the ratio of reactants is not narrowly critical. For best results, however, for each mole of a compound of formula (II), one should employ one mole of a carbonyl chloride of formula (III) to produce one mole of a triester compound of formula (I). It is preferred to employ an excess of a carbonyl chloride of formula (III) for ease of reaction and maximum yield of product. The hydrogen chloride acceptor is preferably used in excess of stoichiometric to insure completeness of reaction.

Due to the reactive nature of the various reaction intermediates and reactants, the process of the present invention should be conducted under essentially anhydrous conditions. Solvents employed in the process of the present invention include such solvents in which an amine hydrochloride, a by-product of the process, is insoluble, such as benzene, toluene, ether and tetrahydrofuran.

While the process of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

A mixture of N-methylene ethylglycinate trimer (5.76 g; 0.05 mol.) and diphenyl phosphite (14.99 g; 0.064 mol.) in benzene was refluxed for one hour and then cooled to 0° C. in an ice bath. To the reaction mixture was added triethylamine (22.8 g; 0.25 mol.) followed by the dropwise addition of a solution of ethylmalonyl chloride (12.84 g; 0.085 mol.) in benzene. The reaction mixture was allowed to warm to 26° C. and then was filtered and the filtrate concentrated in vacuo to yield a yellow oil. The yellow oil was purified using a chromatographic system employing a silica gel column and a 3:2 mixture (by volume) of cyclohexane:ethylacetate as the eluant to yield ethyl-N-(ethoxycarbonylmethylcarbonyl)-N-(diphenoxyphosphinylmethyl)glycinate (2.2 g; 10% yield) represented by the formula

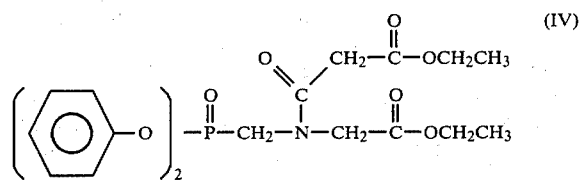

as an oil ($n_D$=1.5433) having the following analysis:
Calculated: C, 57.02; H, 5.66; N, 3.02: Found: C, 57.34; H, 5.87; N, 3.00.

EXAMPLE 2

A mixture of N-methylene ethylglycinate trimer (2.88 g; 0.025 mol.) and di-(4-methoxyphenyl)phosphite (7.97 g; 0.025 mol.) in benzene was refluxed for one hour. Triethylamine (10.1 g; 0.1 mol.) was added to the reaction mixture and the resulting mixture was cooled to 0° C. in an ice bath. A solution of dimethylaminocarbonyl chloride (3.25 g; 0.303 mol.) in benzene was added dropwise to the reaction mixture. The reaction mixture was allowed to warm to 26° C. and then was refluxed for 25 hours. The reaction mixture was filtered and the filtrate concentrated in vacuo producing a crude product. The crude product was purified using a chromatographic system comprising of a silica gel column and a 3:2 mixture (by volume) of ethylacetate:cyclohexane as the eluant to yield ethyl-N-(N',N'-dimethyaminocarbonyl)-N-[bis(4-methoxyphenoxy)phosphinylmethyl]glycinate (3.25 g; 27% yield) represented by the formula

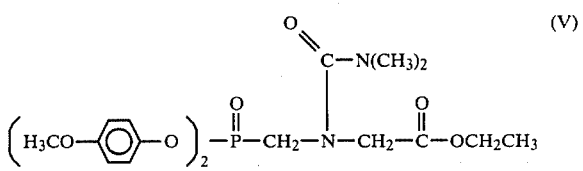

as an oil ($n_D$=1.5327) having the following analysis:

Calculated: C, 53.99; H, 6.18; N, 5.72: Found: C, 53.90; H, 6.20; N, 5.68.

EXAMPLE 3

N',N'-Dipropenylaminocarbonyl chloride (5.6 g; 0.035 mol.) was added to a mixture of ethyl-N-diphenoxyphosphinylmethylglycine (8.4 g; 0.026 mol.) and 1,5-diazabicyclo[5.4.0]undec-5-ene (5.47 g; 0.036 mol.) in 50 ml. of tetrahydrofuran. The reaction mixture was stirred at 26° C. under a nitrogen atmosphere for 64 hours. The reaction mixture was concentrated in vacuo and the resulting residue was diluted with chloroform. The chloroform solution was washed with water, dried over magnesium sulfate and concentrated in vacuo to yield a crude product. The crude product was chromatographically purified employing a silica gel column and a 1:1 mixture (by volume) of cyclohexane:ethylacetate as the eluent to yield an impure product which was then dissolved in ether. The ether solution was washed with a 2% sodium hydroxide solution, water, dried over magnesium sulfate and concentrated in vacuo to yield ethyl-N-[N',N'-dipropenylaminocarbonyl]-N-diphenoxyphosphinylmethylglycinate (2.2 g; 19.3%) represented by the formula

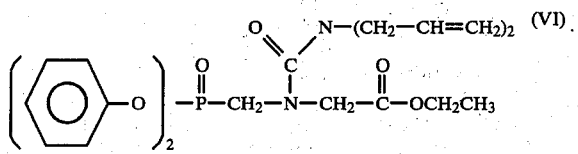

as an oil having the following analysis:

Calculated: C, 61.01; H, 6.19; N, 5.93: Found: C, 60.51; H, 6.36; N, 6.27.

EXAMPLE 4

N'-methyl-N'-4-methylbenzylaminocarbonyl chloride (6.0 g; 0.03 mol.) was added to a mixture of ethyl-N-diphenoxyphosphinylmethylglycinate (6.98 g; 0.012 mol.) and 1,5-diazabicyclo[5.4.0]undec-5-ene (4.56 g; 0.03 mol.) in 50 ml. of tetrahydrofuran. The reaction mixture was stirred at 26° C. under a nitrogen atmosphere for 64 hours. The reaction mixture was concentrated in vacuo and the resulting residue was diluted with chloroform. The chloroform solution was washed with water, dried over magnesium sulfate and concentrated in vacuo to yield a crude product which was then dissolved in ether. The ether solution was washed with 2% sodium hydroxide, water, brine, then dried over magnesium sulfate and concentrated in vacuo to yield a residue. The residue was further purified using a chromatographic system employing a silica gel column and a 3:2 mixture (by volume) of cyclohexane:ethylacetate to yield ethyl-N-[(N'-methyl-N'-4-methylbenzyl-)aminocarbonyl]-N-diphenoxyphosphinylmethylglycinate (0.65 g; 6% yield) represented by the formula

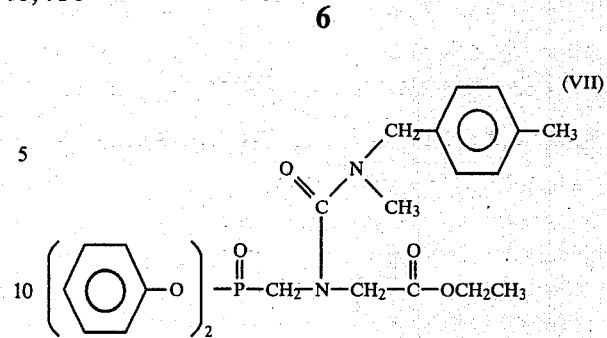

as an oil ($n_D^{27}$=1.5303) having the following analysis:

Calculated: C, 63.52; H, 6.12; N, 5.49: Found: C, 63.27; H, 6.13; N, 5.44.

EXAMPLE 5

A solution of 1,5-diazabicyclo[5.4.0]undec-5-ene (8.30 g; 0.052 mol.) in 50 ml. of tetrahydrofuran was added to a mixture of ethyl-N-diphenoxyphosphinylmethylglycinate (6.98 g; 0.02 mol.) in 50 ml. of tetrahydrofuran. (N'-methyl-N'-benzyl)aminocarbonyl chloride (9.537 g; 0.052 mol.) was added dropwise to the reaction mixture and the mixture was then stirred at 26° C. under nitrogen atmosphere for 192 hours. The reaction mixture was concentrated and the resulting residue was dissolved in chloroform. The chloroform solution was washed with water, brine, dried over magnesium sulfate and concentrated to yield a crude product. The crude product was chromatographically purified employing a silica gel column and a 7:3 mixture (by volume) of cyclohexane:ethylacetate to yield ethyl-N-[(N'-methyl-N'-benzyl)aminocarbonyl]-N-diphenoxyphosphinylmethylglycinate, 1 hydrate (1.45 g; 14% yield) represented by the formula

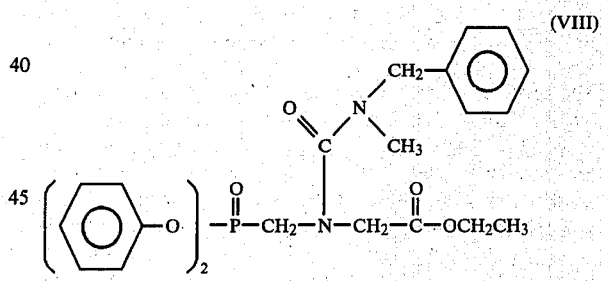

as an oil ($n_D^{25}$=1.538) having the following analysis:

Calculated: C, 60.69; H, 6.07; N, 5.44: Found: C, 60.43; H, 6.06; N, 5.40.

EXAMPLE 6

A mixture of ethyl-N-diphenoxyphosphinylmethylglycinate (6.98 g; 0.02 mol.) and 1,5-diazabicyclo[5.4.0]-undec-5-ene (3.34 g; 0.022 mol.) in 50 ml. of tetrahydrofuran was stirred under a nitrogen atmosphere. To the reaction mixture was dropwise added a solution of N-morpholinocarbonyl chloride (3.25 g; 0.022 mol.) in 5 ml. of tetrahydrofuran. The reaction mixture was stirred at 26° C. for 64 hours. The reaction mixture was concentrated in vacuo and the resulting residue was dissolved in chloroform. The chloroform solution was washed with water and concentrated to yield a crude product. The crude product was chromatographically purified employing a silica gel column and ethylacetate as the eluent to yield ethyl-N-[(N'-morpholino)carbonyl]-N-diphenoxyphosphinylmethylglycinate (3.17 g; 3.4% yield) represented by the formula

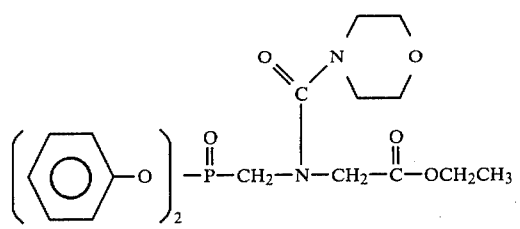

as an oil ($n_D^{27} = 1.5178$) having the following analysis:
Calculated: C, 57.10; H, 5.89; N, 6.06: Found: C, 56.99; H, 5.91; N, 6.02.

EXAMPLE 7

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
| --- | --- |
| 0-24% control | 0 |
| 25-49% control | 1 |
| 50-74% control | 2 |
| 75-99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | Plant Species | | | | |
| --- | --- | --- | --- | --- | --- | --- | --- |
| | | | A | B | C | D | E |
| 1 | 4 | 11.2 | 3 | 2 | 1 | 2 | 2 |
| | 4 | 5.6 | 1 | 2 | 0 | 2 | 1 |
| 2 | 4 | 11.2 | 3 | 3 | 3 | 3 | 3 |
| | 4 | 5.6 | 2 | 2 | 1 | 2 | 3 |
| 3 | 4 | 11.2 | 0 | 1 | 1 | 2 | 3 |
| | 4 | 5.6 | 1 | 1 | 1 | 2 | 3 |
| 4 | 4 | 11.2 | 0 | 1 | 0 | 1 | 3 |
| | 2 | 5.6 | 0 | 0 | 1 | 1 | 1 |
| 5 | 4 | 11.2 | 0 | 1 | 0 | 1 | 1 |
| | 2 | 5.6 | 0 | 1 | 0 | 0 | 0 |
| 6 | 4 | 11.2 | 1 | 2 | 2 | 2 | 4 |
| | 4 | 5.6 | 1 | 2 | 2 | 2 | 2 |

| Compound of Example No. | WAT | kg/h | Plant Species | | | | |
| --- | --- | --- | --- | --- | --- | --- | --- |
| | | | F | G | H | I | J | K |
| 1 | 4 | 11.2 | 2 | 1 | 1 | 1 | 1 | 3 |
| | 4 | 5.6 | 0 | 1 | 0 | 3 | 1 | 3 |
| 2 | 4 | 11.2 | 4 | 1 | 2 | 3 | 3 | 3 |
| | 4 | 5.6 | 1 | 1 | 1 | 0 | 1 | 2 |
| 3 | 4 | 11.2 | 4 | 0 | 1 | 0 | 0 | 2 |
| | 4 | 5.6 | 3 | 1 | 1 | 0 | 0 | 1 |
| 4 | 4 | 11.2 | 1 | 0 | 0 | 1 | 0 | 2 |
| | 2 | 5.6 | 0 | 0 | 0 | 0 | 0 | 1 |
| 5 | 4 | 11.2 | 0 | 0 | 0 | 1 | 0 | 1 |
| | 2 | 5.6 | 0 | 0 | 0 | 0 | 0 | 0 |
| 6 | 4 | 11.2 | 4 | 2 | 1 | 3 | 1 | 4 |
| | 4 | 5.6 | 3 | 2 | 2 | 4 | 2 | 3 |

TABLE II

| Compound of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 1* | 4 | 5.6 | 1 | 0 | 2 | 1 | 2 | 2 | 1 | 2 | 0 | 1 | 2 | 2 | 0 | 1 | 2 | 2 |
| 1* | 2 | 1.12 | 0 | 0 | 0 | 0 | 0 | 0 | 0 | 1 | 0 | 1 | 0 | 0 | 0 | 0 | 0 | 0 |
| 1* | 2 | 0.25 | 0 | 0 | 0 | 0 | 0 | 0 | 0 | 0 | 0 | 0 | 0 | 0 | 0 | 0 | 0 | 0 |
| 2 | 4 | 5.6 | 2 | 2 | 2 | 1 | 4 | 3 | 2 | 2 | 2 | 2 | 3 | 3 | 3 | 4 | 3 | 4 |
| 2 | 4 | 1.12 | 1 | 1 | 1 | 0 | 2 | 2 | 1 | 2 | 1 | 1 | 1 | 1 | 1 | 2 | 1 | 3 |
| 2 | 4 | 0.25 | 1 | 0 | 0 | 0 | 1 | 0 | 0 | 1 | 0 | 0 | 0 | 1 | 0 | 0 | 0 | 1 |
| 3 | 4 | 5.6 | 1 | 3 | 2 | 1 | 2 | — | 1 | 3 | 2 | 2 | 2 | 1 | 2 | 4 | 3 | 4 |
| 3 | 4 | 1.12 | 0 | 0 | 1 | 0 | 1 | 0 | 0 | 0 | 0 | 0 | 0 | 0 | 0 | 2 | 1 | 2 |
| 3 | 2 | 0.28 | 0 | 0 | 0 | 0 | 0 | 0 | 0 | 1 | 1 | 0 | 0 | 0 | 0 | 0 | 0 | 0 |
| 6 | 4 | 5.6 | 0 | 3 | 3 | 1 | 4 | 2 | 3 | 2 | 1 | 3 | 3 | 1 | 3 | 4 | 3 | 4 |
| 6 | 4 | 1.12 | 0 | 1 | 1 | 0 | 3 | 1 | 1 | 1 | 0 | — | 4 | 0 | 1 | 3 | 2 | 3 |

TABLE II-continued

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 6 | 2 | 0.28 | 0 | 0 | 0 | 0 | 0 | 0 | 1 | 0 | 0 | 0 | 0 | 0 | 0 | 0 | 0 | 0 |

*formulated just prior to spraying

It should be noted that the compounds prepared in Examples 1 and 2 also exhibited pre-emergent herbicidal activity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylophenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

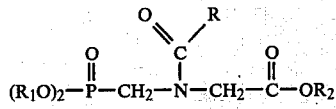

wherein R is a

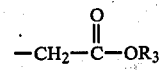

group wherein $R_3$ is lower alkyl, $R_1$ is phenyl or lower alkoxyphenyl; and $R_2$ is lower alkyl.

2. A compound according to claim 1 wherein $R_2$ is ethyl.

3. A compound according to claim 2 wherein $R_1$ is phenyl.

4. A compound according to claim 3 which is ethyl-N-(ethoxycarbonylmethylcarbonyl)-N-(diphenoxyphosphinylmethyl)glycinate.

5. A herbicidal composition comprising an inert adjuvant and a herbicidally effective amount of a compound of the formula

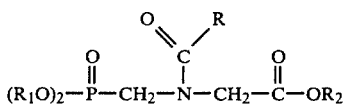

wherein R is a

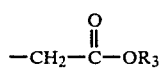

group wherein $R_3$ is lower alkyl, $R_1$ is phenyl or lower alkoxyphenyl; and $R_2$ is lower alkyl.

6. A composition according to claim 5 wherein $R_2$ is ethyl.

7. A composition according to claim 6 wherein $R_1$ is phenyl.

8. A composition according to claim 7 wherein the compound is an ethyl-N-(ethoxycarbonylmethylcarbonyl)-N-(diphenoxyphosphinylmethyl)glycinate.

9. A method of controlling undesired plants which comprises contacting said plants with a herbicidal amount of a compound of the formula

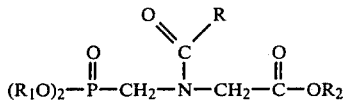

wherein R is a

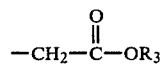

group wherein $R_3$ is lower alkyl, $R_1$ is phenyl or lower alkoxyphenyl; and $R_2$ is lower alkyl.

10. A method according to claim 9 wherein $R_2$ is ethyl.

11. A method according to claim 10 wherein $R_1$ is phenyl.

12. A method according to claim 11 wherein the compound is ethyl-N-(ethoxycarbonylmethylcarbonyl)-N-(diphenoxyphosphinylmethyl)glycinate.

* * * * *